US00PP32304P3

(12) United States Plant Patent
Cain

(10) Patent No.: US PP32,304 P3
(45) Date of Patent: Oct. 13, 2020

(54) GRAPEVINE PLANT NAMED 'IFG THIRTY-EIGHT'

(50) Latin Name: *Vitis vinifera*
Varietal Denomination: IFG Thirty-eight

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 25 days.

(21) Appl. No.: 16/350,653

(22) Filed: Dec. 21, 2018

(65) Prior Publication Data

US 2020/0205328 P1 Jun. 25, 2020

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207, 205
CPC ..... A01H 5/0812; A01H 5/08; A01H 5/02; A01H 5/0806; A01H 6/88; A01H 5/12; A01H 6/78
See application file for complete search history.

(56) References Cited

U.S. PATENT DOCUMENTS

PP21,664 P3 1/2011 Cain
PP24,611 P3 7/2014 Cain

*Primary Examiner* — June Hwu

(57) ABSTRACT

This invention is a new and distinct grapevine variety denominated 'IFG Thirty-eight'. The new grapevine is characterized by producing medium size round white berries having crisp texture with a very strong muscat flavor and which ripens in midseason. Berries are borne on medium size clusters which are compact.

1 Drawing Sheet

Latin name of the genus and species claimed: *Vitis vinifera.*

Variety denomination: 'IFG Thirty-eight'.

BACKGROUND OF THE INVENTION

The new and distinct Grapevine plant described and claimed herein originated from a hand pollinated cross of 'IFG 68-175' (U.S. Plant Pat. No. 21,664), and 'IFG Fourteen' (U.S. Plant Pat. No. 24,611), hybridized in May 2009. The abortive seed traces were subsequently embryo cultured and the resulting 144 plants were planted in the field in April 2010. The present variety of grapevine was selected as a single plant in July 2012 and was first asexually propagated by hardwood cuttings in December 2012 near Delano, Kern County, Calif. These resulting cuttings produced second generation plants that were planted during April 2013 near Delano, Kern County, Calif. and were observed for five years and found to reproduce true-to-type.

BRIEF SUMMARY OF THE INVENTION

The new grapevine 'IFG Thirty-eight' is characterized by producing medium sized round white berries having crisp texture with a very strong muscat flavor and which ripens in midseason. Berries are borne on medium size clusters which are compact and gibberellin applications are necessary to thin clusters and size berries. 'IFG Thirty-eight' stores well. Stems remain green and berries retain their crisp texture and strong muscat flavor for up to eight weeks in cold storage. To the inventor's knowledge, the known variety to which the new grapevine variety is most similar is the Perlette variety (unpatented). 'IFG Thirty-eight' differs from the 'Perlette' by ripening approximately two to three weeks later, and having a very strong muscat flavor as opposed to the neutral to very mild muscat flavor of 'Perlette' and by having naturally larger berries than 'Perlette'.

'IFG Fourteen' differs from its maternal parent, 'IFG68-175' by producing medium size white berries that have a strong muscat flavor as opposed to the larger, neutral flavored red berries of 'IFG 68-175'. It differs from its pollen parent, 'IFG Thirty-eight' by having white berries as opposed to the red berries of 'IFG Fourteen' and by having a larger broader cluster.

BRIEF DESCRIPTION OF THE DRAWING

The accompanying photographic drawing in FIG. 1 illustrates in full color 'IFG Thirty-eight', taken from a 4-year-old vine. The photograph was taken outdoors with indirect lighting. The colors are as nearly true as is reasonably possible in a color representation of this type. The left side of the drawing has a mature leaf. A mature fruit cluster is represented in the center of the drawing along with a typical berry in cross section. A young shoot tip can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2015 by The Royal Horticultural Society, London, England.

Throughout this specification, subjective description values conform to those set forth by the UPOV International Union for the Protection of New Varieties of Plants publication 'Grapevine *Vitis* L. Guidelines'.

The descriptive matter which follows pertains to 4-year-old plants of 'IFG Thirty-eight' plants grown in the vicinity of Delano, Kern County, Calif. during 2017 and 2018, and is believed to apply to plants of the variety grown under similar conditions of soil and climate elsewhere:

VINE

General:

*Vigor*.—Vigorous.
*Density of foliage*.—Dense.
*Productivity*.—Productive, producing about 21.1 to 31.6 kg of fruit per vine.
*Root stock*.—Own root.
*Training method*.—Typically spur pruned leaving 2 bud spurs.
*Plant hardiness zone*.—Fully hardy in USDA zone 9A (2012). Not tested in other zones.

Trunk:

*Trunk diameter of* 4-*year-old vines at* 30 *cm above the soil line*.—About 5.9 cm.
*Shape*.—Medium.
*Straps*.—Very long, Continuous.
*Surface texture*.—Shaggy texture.
*Inner bark color*.—The following colors were observed: Greyed-orange: 166A and 166B.
*Outer bark color*.—The following colors were observed: Brown: N200B and N200C.

SHOOTS

Young shoot:

*Form of tip*.—Fully opened.
*Distribution of anthocyanin coloration of tip*.—Absent.
*Intensity of anthocyanin coloration of tip*.—Absent.
*Density of prostrate hairs of tip*.—Sparse.
*Density of erect hairs on tip*.—Absent.
*Color*.—Yellow-green: 144B.

Woody shoot (mature canes):

*Internode length*.—Long: About 16.5 cm.
*Width at node*.—About 1.6 cm.
*Cross section*.—Circular to slightly elliptic.
*Surface*.—Striate.
*Main color*.—The following colors were observed: Greyed-orange: 165A and 165B and 165C.
*Density of erect hairs on nodes*.—Very sparse.
*Density of erect hairs on internodes*.—None.

Flowering shoot:

*Vigor during flowering*.—Medium to strong.
*Attitude during flowering on shoots not tied*.—Semi-erect.
*Color*.—Dorsal side of internodes — Yellow-green: 144B.
*Color*.—Ventral side of internodes — Yellow-green: 144B.
*Color*.—Dorsal side of nodes — Yellow-green: 144B, with Greyed-purple stripes: 184A.
*Color*.—Ventral side of nodes — Yellow-green: 144B.
*Density of prostrate hairs on nodes*.—Very sparse.
*Density of erect hairs on nodes*.—None.
*Density of prostrate hairs on internode*.—Very sparse.
*Density of erect hairs on internode*.—None.
*Anthocyanin coloration of buds*.—Absent.

Tendrils:

*Distribution on the shoot* (*at full flowering*).—Discontinuous.
*Length of tendril*.—Long: About 22.5 cm.
*Thickness of tendril* 2 *cm from base*.—About 1.6 mm.
*Color*.—Yellow-green: 144A.
*Form*.—Trifurcated.
*Number of consecutive tendrils*.—2.

LEAVES

Young leaves:

*Color of upper surface of first four distal unfolded leaves*.—Yellow-green: 144A and 144B.
*Color of lower surface of young leaves*.—Yellow-green: 144B.
*Average intensity of anthocyanin coloration of six distal leaves prior to flowering*.—Absent.
*Density of prostrate hairs between veins* (*lower surface*).—Absent to very sparse.
*Density of prostrate hairs on veins* (*lower surface*).—Very sparse.
*Density of erect hairs between veins* (*lower surface*).—Absent.
*Density of erect hairs on veins* (*lower surface*).—Very sparse.

Mature leaves (opposite first cluster):

*Average length*.—About 19.1 cm.
*Average width*.—About 13.9 cm.
*Mature leaf size*.—Large.
*Shape of blade*.—Wedge-shaped.
*Number of lobes*.—5.
*Blade venation*.—Palmate.
*Anthocyanin coloration of main veins on upper side of blade*.—Absent.
*Mature leaf profile*.—Undulate.
*Leaf blade tip*.—In the horizontal plane of the leaf mid-vein. Does not appear to curve downward.
*Leaf apex*.—Broadly acute.
*Leaf margin*.—Serrate.
*Undulation of margin*.—Slight.
*Undulation of blade between main and lateral veins*.—Slight undulation over entire area.
*Shape of teeth*.—Mixture of both sides straight and both sides convex.
*Length of teeth*.—Medium to long.
*Ratio length/width of teeth*.—Medium.
*Shape of upper lateral sinuses*.—Lobes strongly overlapping.
*Depth of upper lateral sinuses*.—Deep.
*General shape petiole sinus*.—Mixture of lobes slightly and strongly overlapping.
*Shape of base of upper leaf sinuses*.—V-shaped.
*Tooth at petiole sinus*.—Absent.
*Density of prostrate hairs between veins on lower surface of blade*.—Very sparse.
*Density of erect hairs between veins on lower surface of blade*.—Very sparse.
*Density of prostrate hairs on main veins on lower surface of blade*.—Very sparse.

*Density of erect hairs on main veins on lower surface of blade*.—Sparse to medium.
*Density of prostrate hairs on main veins on upper surface of blade*.—Sparse.
*Density of erect hairs on main veins on upper surface of blade*.—Very sparse.
*Autumn coloration of leaves*.—The following colors were observe: Greyed-yellow: 162A and 162B and 162C.

Upper surface:
*Color*.—Green: 137A.
*Anthocyanin coloration of main veins* (*lower surface*).—Absent.
*Color of main veins*.—Yellow-green: 144C.
*Surface appearance*.—Semi-glossy.
*Blistering surface of blade*.—Medium.

Lower surface:
*Color*.—Yellow-green: 146B.
*Anthocyanin coloration of main veins* (*lower surface*).—Absent.
*Color of main veins*.—Yellow-green: 145C.
*Glossiness*.—Weak.
*Surface texture*.—Rugose.
*Surface appearance*.—Dull.

Petiole:
*Length*.—About 13.2 cm.
*Diameter of petiole* 2 *cm from blade*.—About 4.2 mm.
*Petiole color*.—The following colors were observed: Yellow-green: 145B and Greyed-purple: 186B.
*Length of petiole compared to middle vein*.—Slightly shorter.
*Density of prostrate hairs on petiole*.—None or very sparse.
*Density of erect hairs on petiole*.—None or very sparse.

Buds:
*Bud fruitfulness*.—Basal: mostly fruitful.
*Position of first fruitful shoot on previous season cane*.—$1^{st}$ to $2^{nd}$ node.
*Dormant bud length*.—About 6.0 mm.
*Dormant bud width in the proximal/distal plane*.—About 4.6 mm.
*Dormant bud color*.—Greyed-orange: 166A.
*Time of bud burst*.—Early: Approximately Mar. 8, 2018.

FLOWERS

General:
*Flower sex*.—Hermaphrodite.
*Length of single flower, unopened*.—About 2.1 mm.
*Width of single flower*.—Unopened: About 3.0 mm. Opened: About 7.4 mm.
*Stamen length*.—About 3.5 mm.
*Stamen count*.—5.
*Pollen color*.—Yellow: 10B.
*Pistil length*.—About 2.5 mm.
*Pistil color*.—Yellow-green: 144A.
*Position of first flowering and fruiting node*.—$4^{th}$ to $5^{th}$ node (current season growth).
*Number of inflorescence per flowering shoot*.—1.
*Time of bloom*.—Early as compared with similar varieties in the growing area of Delano, Calif.
*Date of full bloom*.—About May 7, 2018.

FRUIT

General:
*Ripening period*.—Early: Approximately Jul. 20, 2018.
*Use*.—Fresh market.
*Keeping quality*.—Average, may exhibit surface discoloration.
*Resistance/susceptibility to typical pests and diseases of vitis vinifera species*.—Not observed to date.
*Refractometer test*.—Soluble solids: About 18.2 Brix.
*Brix/acid*.—About 39.6.
*Titratable acidity*.—About 0.46.
*Juice pH*.—About 3.68.
*Juice color*.—Yellow-green: 144D.

Cluster:
*Mature cluster length* (*peduncle excluded*).—About 19.3 cm.
*Mature cluster width*.—About 17.2 cm.
*Mature cluster weight*.—About 702.5 g.
*Bunch density*.—Medium to compact.
*Number of berries*.—About 153.
*Form*.—Conical.

Peduncle:
*Lignification of peduncle*.—Weak.
*Diameter of peduncle*.—About 5.4 mm.
*Length of peduncle*.—Short: Approximately 2.6 cm.
*Color of peduncle*.—Yellow-green: 145A.

Berry:
*Uniformity of size*.—Uniform.
*Single berry weight*.—About 5.9 g.
*Shape*.—Globose.
*Seeds*.—Contains small rudimentary seed traces.
*Cross section*.—Circular.
*Berry dimensions*.—Longitudinal axis: About 2.1 cm. Horizontal axis: About 2.1 cm.
*Pedicel length*.—About 10.7 mm.
*Pedicel width*.—About 1.8 mm.
*Pedicel color*.—Yellow-green: 145A.
*Berry firmness*.—Firm.
*Particular flavor*.—Muscat.
*Bloom* (*cuticular wax*).—Weak.
*Berry separation from pedicel*.—Difficult.
*Skin color* (*without bloom*).—Yellow-green: 145B.
*Flesh color*.—Yellow-green: 145B.
*Anthocyanin coloration of flesh*.—Absent.

Skin:
*Thickness*.—Medium.
*Skin toughness*.—Somewhat notable when chewing.
*Reticulation*.—Absent.
*Tenacity*.—Tenacious to flesh.

What is claimed:

1. A new and distinct variety of grapevine as herein illustrated and described.

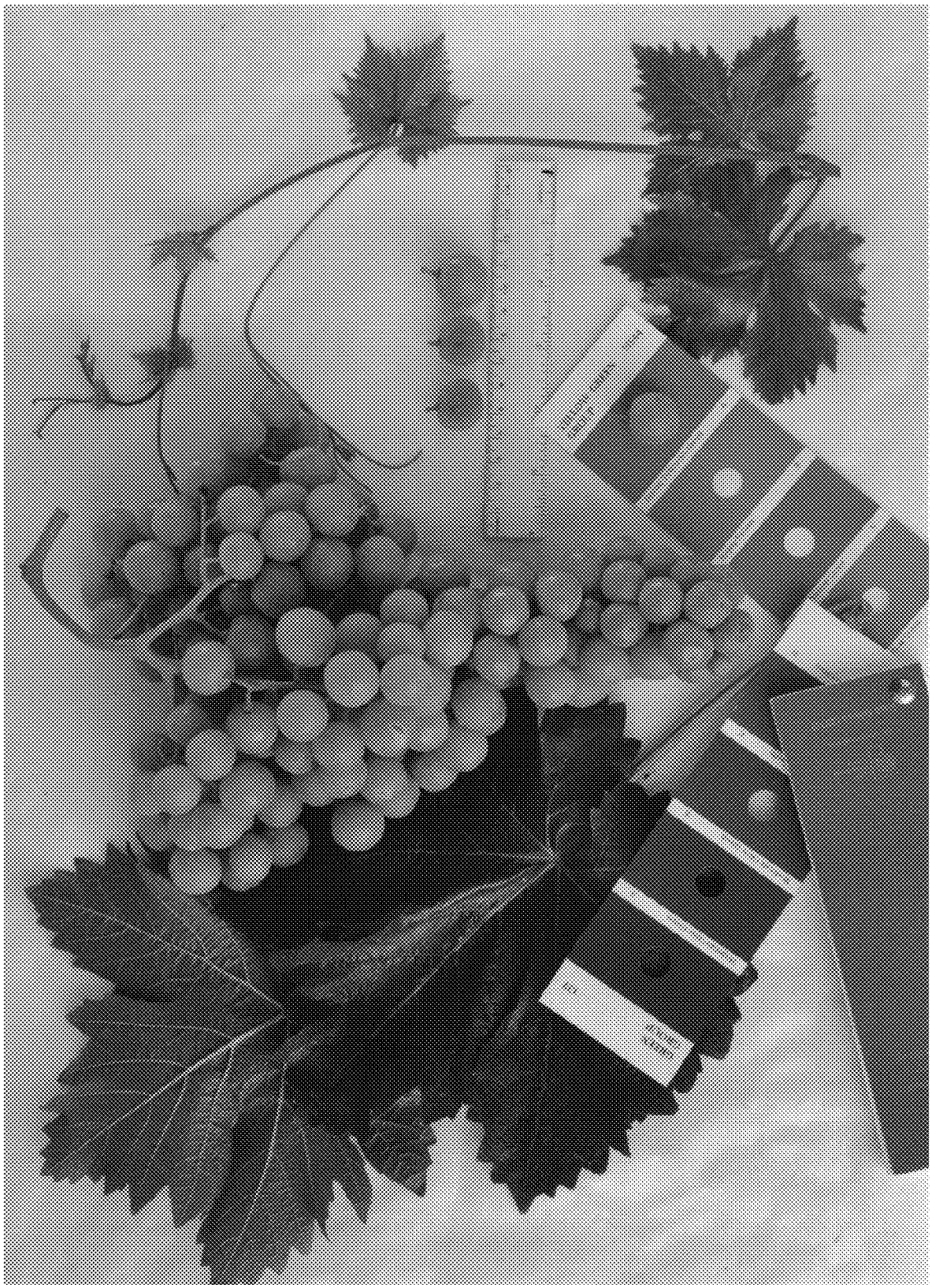

* * * * *